United States Patent [19]

Tanaka et al.

[11] 4,056,547
[45] Nov. 1, 1977

[54] PROCESS FOR THE PREPARATION OF ORGANIC ISOCYANATE COMPOUNDS

[75] Inventors: Yoshiaki Tanaka, Osaka; Susumu Handa, Wakayama; Atsushi Nishibata, Wakayama; Sadashi Ueda, Wakayama; Yoshiaki Inamoto, Wakayama; Masahiro Saito, Wakayama; Fumio Tanimoto, Kyoto; Hisao Kitano, Osaka, all of Japan

[73] Assignee: Kao Soap Co., Ltd., Tokyo, Japan

[21] Appl. No.: 726,205

[22] Filed: Sept. 24, 1976

[30] Foreign Application Priority Data

Oct. 7, 1975 Japan .................................. 50-121047

[51] Int. Cl.$^2$ ............................................ C07C 118/00
[52] U.S. Cl. ................................. 260/453 P; 544/221
[58] Field of Search ...................................... 260/453 P

[56] References Cited

U.S. PATENT DOCUMENTS

| | | | |
|---|---|---|---|
| 2,866,802 | 12/1958 | Graham ............................. | 260/453 P |
| 2,866,803 | 12/1958 | de Pree ............................. | 260/453 P |
| 3,558,684 | 1/1971 | von Brachel et al. ............. | 260/453 P |
| 3,816,499 | 6/1974 | Beswick et al. .................. | 260/453 P |

*Primary Examiner*—Dolph H. Torrence

*Attorney, Agent, or Firm*—Blanchard, Flynn, Thiel, Boutell & Tanis

[57] ABSTRACT

A process for preparing organic isocyanate compounds characterized by reacting a chloromethyl group-containing compound having the formula:

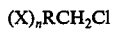

$(X)_n RCH_2Cl$ wherein X, which can be the same or different, is chlorine, alkyl, cycloalkyl, alkenyl, phenyl, chloromethylphenyl or chloromethyl, n is 0 or an integer of 1 to 3, and R is an aromatic hydrocarbon radical or an olefin radical, with an alkali cyanate, in the presence of a catalyst composition comprising (a) a cuprous salt in an amount of 0.1 to 20% by weight, based on said chloromethyl group-containing compound, and (b) a tertiary amine compound or quaternary ammonium compound in an amount equivalent to 0.05 to 1.25 gram atoms of nitrogen per gram mole of said cuprous salt, in a high-boiling-point solvent having a dieelectric constant ($\epsilon$) not higher than 20, at a reaction temperature of 150° to 250° C, for 0.1 to 10 hours.

4 Claims, 2 Drawing Figures

PROCESS FOR THE PREPARATION OF ORGANIC ISOCYANATE COMPOUNDS

BACKGROUND OF THE INVENTION

1. Field of the Invention

The present invention relates to a process for preparing isocyanatomethyl group-containing compounds by using a unique catalyst composition.

It is a primary object of the present invention to prepare, easily and economically, isocyanate compounds which are valuable as starting materials for the preparation of polyurethane materials, polyurea materials, polyisocyanurate materials and the like, all of which are valuable materials used widely in chemical industries, resin industries, paint industries and other industrial fields.

2. Description of the Prior Art

Various processes for the preparation of isocyanate compounds are known in the art. As an industrially important process, there can be mentioned a process in which an isocyanate is prepared from an amine or amine salt and a phosgene. Recently, a process for preparing an isocyanate from a nitro compound and carbon monoxide has been studied. Further, the reaction between an alkali cyanate and an organic halide has been known and studied for many years. This process was not very successful until so-called aprotic solvents such as DMF (dimethylformamide), DMSO (dimethylsulfoxide) or the like were developed. In 1957, Fukui et al found that isocyanuric acid esters and isocyanic acid esters, in some cases, can easily by synthesized under mild conditions in such an aprotic solvent, and since then, various compounds have been prepared by similar reactions. As processes using a catalyst in a non-protonic solvent, other than aprotic solvents, there can be mentioned, for example, a process using a tertiary amine or quaternary ammonium salt as a catalyst (U.S. Pat. No. 2,866,802), a process using a catalyst composition of phosphorus pentoxide and a weakly basic organic tertiary nitrogen compound (Japanese Patent Application Laid-Open Specification No. 36149/73) and a process for preparing an isocyanate from an α,β-alkenyl halide in the presence of copper or a cuprous salt as a catalyst (U.S. Pat. No. 3,558,684). Generally speaking, the process of the present invention belongs to the latter type.

In the synthesis process for isolating an isocyanic acid ester by using a tertiary amine or quaternary ammonium salt as a catalyst, the catalyst is deactivated during the reaction and it is difficult to complete the reaction. Further, the amount of isocyanurate formed as a by-product increases as the reaction advances and the yield of the intended isocyanate is reduced. In the process using copper or a cuprous salt as a catalyst, it takes several to ten or more hours to complete the reaction, and in some cases, the starting halide is not completely consumed. Further as the reaction is extended, the amount of isocyanurate formed as a by-product increases and the yield of the desired isocyanate is drastically reduced. Another defect of this process is that because the boiling points of the starting halide and the desired isocyanate are very close to each other, if the halide is present, it is very difficult to separate the product from the starting halide. For this reason, the reaction must be essentially completed.

SUMMARY OF THE INVENTION

In accordance with the present invention, there is provided a process for preparing isocyanate compounds by reacting a chloromethyl group-containing compound having the formula:

$(X)_nRCH_2Cl$ wherein X, which can be the same or different, is alkyl, especially alkyl having one to 12 carbon atoms, cycloalkyl, especially cycloalkyl having 3 to 7 carbon atoms, alkenyl, especially alkenyl having 2 to 12 carbon atoms, phenyl, chloromethylphenyl or chloromethyl, n is 0 or an integer of 1 to 3, and R is an aromatic hydrocarbon radical, especially phenyl or phenyl substituted by X, naphthalene, or an olefin radical, especially mono-olefinically unsaturated hydrocarbon radical having 2 to 6 carbon atoms, substituted or not substituted with X, preferably vinyl or —CH=C(CH$_3$)—, with an alkali cyanate, in the presence of a catalyst composition comprising (a) a cuprous salt in an amount of 0.1 to 20% by weight based on the weight of said chloromethyl group-containing compound and (b) a tertiary amine compound or quarternary ammonium compound in an amount equivalent to 0.05 to 1.25 gram atoms of nitrogen per gram mole of said cuprous salt, in a high-boiling-point solvent having a dielectric constant (ε) not higher than 20, at a reaction temperature of 150° to 250° C, for 0.1 to 10 hours.

In the present invention, a catalyst composition comprising a cuprous salt and a tertiary amine compound or quarternary ammonium salt, at a specific ratio, is used for reacting an organic halide with an alkali cyanate, in a solvent having a low polarity (ε ≦ 20). This specific ratio of the two components in the combination catalyst is a critical feature of the present invention. Namely, the present invention is characterized in that the nitrogen compound is used in an amount equivalent to 0.05 to 1.25 gram atoms of nitrogen per gram mole of the cuprous salt used. When a catalyst having this specific combination ratio is employed, the reaction is completed very quickly, and formation of the unwanted isocyanurate, which is a main by-product, is remarkably reduced and an isocyanate (isocyanic acid ester) is substantially selectively formed, as illustrated in the Examples given hereinafter. This is surprising and is unobvious in view of the above-mentioned disclosures in U.S. Pat. Nos. 2,866,802, 2,866,803 and 3,558,684. The above characteristic feature of the present invention cannot be anticipated by combining the teachings of these prior art references.

In the present invention, there can be used not only a composition of one copper compound and one nitrogen compound, but also a composition including a plurality of copper compounds and/or a plurality of nitrogen compounds, provided that the total amounts of copper and nitrogen are within the above range specified in the present invention.

As the alkali cyanate that is used in the present invention, there can be mentioned lithium cyanate, sodium cyanate, potassium cyanate and ammonium cyanate. These salts may be used singly or in the form of a mixture of two or more of them. From the industrial viewpoint, the use of sodium cyanate and potassium cyanate is especially preferred. If the purity of the alkali cyanate is higher than 70%, no particular disadvantage is brought about in the process of the present invention. Accordingly, alkali cyanates of an industrial grade can be used satisfactorily in the present invention.

As the cuprous salt that is used in the present invention, there can be mentioned cuprous chloride, cuprous bromide, cuprous thiocyanate, cuprous cyanate and mixtures thereof. Typical examples of the tertiary amine and quaternary ammonium salt used in combination with the cuprous salt include triethylene diamine, pyridine, ethylpyridine, lutidine, collidine, trimethylamine, triethylamine, tripropylamine, tributylamine, triamylamine, trihexylamine, tri-higher-alkylamines, dimethylbenzylamine, methyldibenzylamine, tribenzylamine, dimethylnaphthylamine, N-methylpiperidine, N-methylmorpholine, N-butylmorpholine, N,N'-dimethylpiperazine, tetramethylammonium chloride, tetraethylammonium chloride, trimethylbenzylammonium chloride, dimethylbenzyl-higher-alkyl-ammonium chloride, tetramethylammonium bromide, tetraethylammonium bromide, trimethylbenzylammonium bromide, 1,8-diaza bicyclo[5.4.0]-7-undecene and mixtures thereof.

As the high-boiling-point solvent having a low polarity (dielectric constant $\epsilon \leq 20$), there are employed organic solvents which are free of an active hydrogen atom, which having a boiling point of 150° to 400° C under atmospheric pressure and which have a good heat stability. Typical examples include high-boiling-point petroleum hydrocarbon oils, high-boiling-point coal tar hydrocarbon oils, higher alkyl ethers, higher alkyl ketones, phosphoric acid esters, tetralin, decalin, higher alkyl benzenes, polyalkyl benzenes, alkyl naphthalenes, polyalkyl naphthalenes, diphenyl ethers, alkylphenyl ethers, benzophenones, alkylphenyl ketones, diphenyl, terphenyl, dichlorobenzene, dibromobenzene, trichlorobenzene, dichloronaphthalene, trichloronaphthalene, polychlorobiphenyls, glycol higher alkyl ethers and polyalkylene glycol dialkyl ethers. These solvents can be used singly or in the form of a mixture of two or more of them.

Typical examples of the chloromethyl group-containing compound that is used in the present invention (prefixes such as ortho, meta and para are omitted in order to avoid unnecessary complication; all such isomers are included in the invention) include benzyl chloride, chlorobenzyl chloride, methylbenzyl chloride, ethylbenzyl chloride, vinylbenzyl chloride, phenylbenzyl chloride, chloromethylphenylbenzyl chloride, chloromethylnaphthalene, bischloromethylnaphthalene, cyclohexylbenzyl chloride, xylylene dichloride, chloroxylylene dichloride, methylxylylene dichloride, dichloroxylylene dichloride, dimethylxylylene dichloride, methylchloroxylylene dichloride, dimethyldichloroxylylene dichloride, allyl chloride, methallyl chloride, crotyl chloride, 1-chloro-2-methylbutene-2, 1,4-dichlorobutene-2, 3,4-dichlorobutene-1, 1,4-dichloro-2-methylbutene-2, 1-chloropentene-2 and 1-chlorohexene-2. These compounds are free of atoms of elements other than hydrogen, carbon and chlorine.

In practicing the process of the present invention, it is necessary to perform the reaction at a temperature of 150° to 250° C, for from 0.1 to 10 hours. If these conditions are not satisfied, the yield of the desired product is reduced or the desired product cannot be obtained at all. According to the present invention, isocyanate compounds can be prepared very easily in a specific solvent under the above reaction condition in high yields with economic advantages.

We made various experiments on the above-illustrated process of the present invention and confirmed the excellence of the present invention based on these experiments. Accordingly, typical experiments sufficient to illustrate the technical content of the present invention are derived from these various experiments and are described as Examples. Accordingly, it must be noted that the present invention is not limited by these Examples and various modifications can be made within the purport and spirit of the present invention.

EXAMPLE 1

A reaction vessel equipped with an agitator, a reflux cooler and a thermometer was charged with 12.7 g of sodium cyanate having a purity of 100%, 66 g of o-dichlorobenzene and 19 g of benzyl chloride, and the mixture was heated under a nitrogen atmosphere. Then, 1.5 g of freshly prepared cuprous chloride and 0.42 g of triethylene diamine were added to the mixture, and the reaction was carried out at 180° C for 45 minutes. The inorganic salts were removed by filtration and the filtrate was analyzed. It was found that 19.1 g (95.8%) of benzyl isocyanate and 0.4 g (1.8) of tribenzyl isocyanurate were formed and 0.46 g (2.4%) of benzyl chloride was left unreacted in the reaction mixture.

EXAMPLE 2

In the same manner as described in Example 1, 13.4 g of sodium cyanate having a purity of 95%, 19 g of benzyl chloride, 1.5 g of cuprous chloride and 0.42 g of triethylene diamine were reacted at 180° C for 30 minutes in 66 g of benzophenone as a solvent. From the results of the analysis of the filtrate recovered from the reaction mixture, it was found that the filtrate comprised 18.1 g (90.9%) of benzyl isocyanate, 1.3 g (6.6%) of tribenzyl isocyanurate and 0.5 g (2.5%) of the unreacted benzyl chloride.

EXAMPLE 3

In the same manner as described in Example 1, 38 g of benzyl chloride, 24.7 g of potassium cyanate having a purity of 100%, 3.0 g of cuprous chloride and 2.8 g of tri-n-butylamine were reacted at 180° C for 1 hour in 120 ml of o-dichlorobenzene as a solvent. From the results of the analysis of the filtrate recovered from the reaction mixture, it was found that the filtrate comprised 34.7 g (87%) of benzyl isocyanate, 4.0 g (10%) of tribenzyl isocyanurate and 1.1 g (3%) of the unreacted starting chloride.

EXAMPLE 4

The reaction was conducted at 180° C for 30 minutes in the same manner as described in Example 1 except that 1.4 g of trimethylbenzylammonium chloride was used instead of 0.42 g of triethylene diamine. From the results of the analysis of the filtrate recovered from the reaction mixture, it was found that the filtrate comprised 81% of benzyl isocyanate, 5% of tribenzyl isocyanurate and 14% of the unreacted starting benzyl chloride.

EXAMPLE 5

Figure 1:
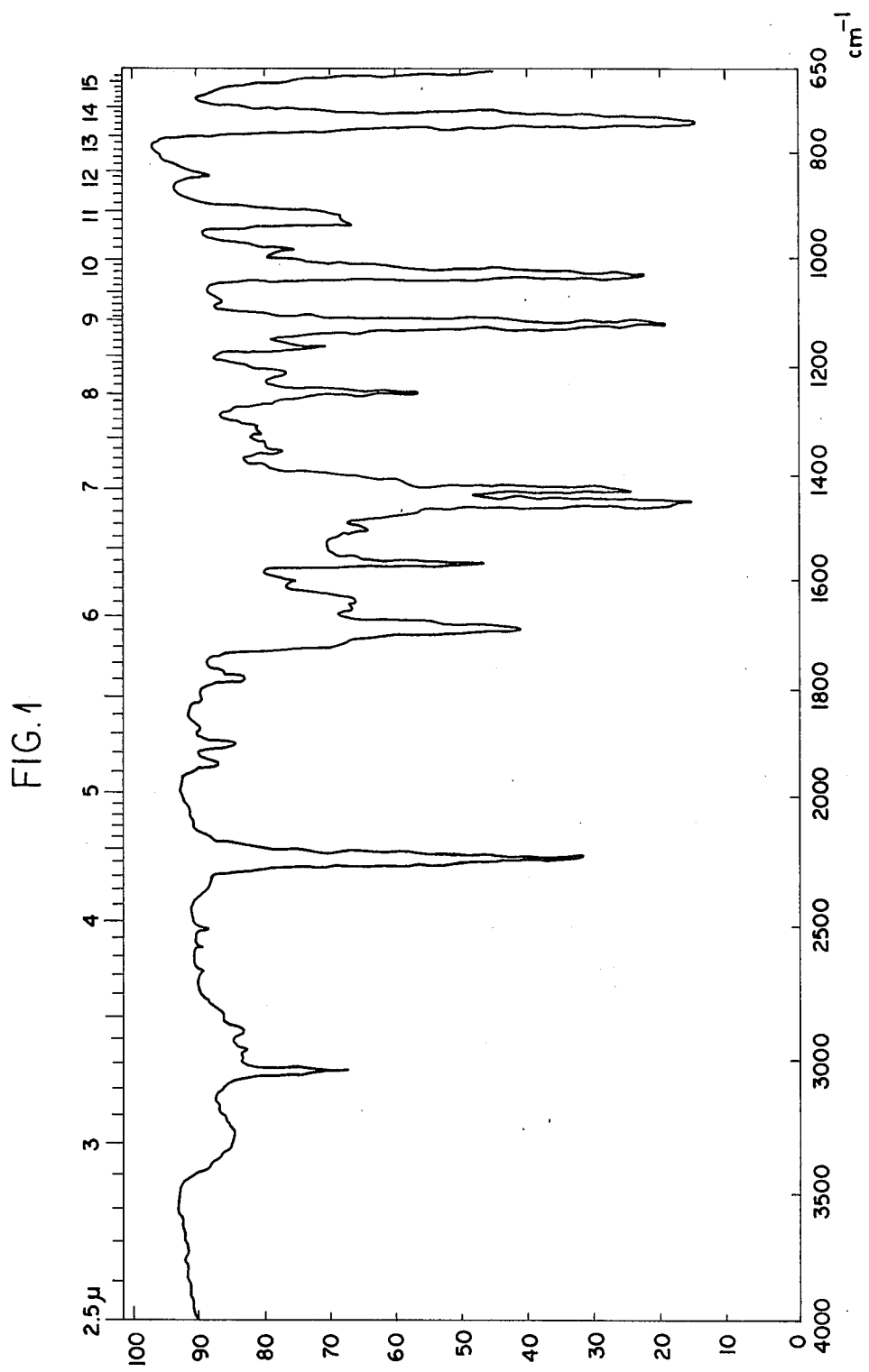
FIG. 1 is the infrared absorption spectrum of the product obtained in Example 5.

A 300 ml-capacity stainless steel pressure vessel equipped with an agitator was charged with 15.3 g of allyl chloride, 13.0 g of sodium cyanate having a purity of 100%, 88.2 g of o-dichlorobenzene, 1.98 g of cuprous chloride and 0.56 g of triethylene diamine. After sealing the vessel and with agitation, the temperature was elevated to 180° C over a period of 20 minutes, and the temperature was maintained at 180° ± 2° C for 1 hour, followed by cooling. The reaction was conducted under an atmosphere of dry nitrogen. The resulting reaction mixture was quickly filtered to remove the inorganic salts. When the filtrate was analyzed by gas chromatography, it was found that the filtrate comprised 91.4% of allyl isocyanate, 1.6% of the unreacted starting allyl chloride and 7.0% of triallyl isocyanurate. The infrared absorption spectrum of the reaction product is shown in FIG. 1, in which a sharp absorption owing to the isocyanate group is observed at 2250 cm$^{-1}$.

EXAMPLE 6

In the same manner as described in Example 1, 57 g of benzyl chloride, 29.4 g of sodium cyanate having a purity of 100%, 4.5 g of cuprous chloride and 1.26 g of triethylene diamine were reacted at 180° C for 1.5 hours in 200 g of decalin as a solvent. The inorganic salts were removed from the reaction mixture by filtration and the filtrate was analyzed. It was found that the filtrate comprised 80.3% of benzyl isocyanate, 19% of tribenzyl isocyanurate and 9.7% of the unreacted benzyl chloride.

COMPARATIVE EXAMPLE 1

In the same manner as described in Example 1, 19 g of benzyl chloride and 12.7 g of sodium cyanate having a purity of 100% were reacted at 180° C under agitation in 66 g of o-dichlorobenzene in which 1.5 g of cuprous chloride had been incorporated.

The composition of the filtrate recovered from the reaction mixture was as shown in Table 1.

Table 1

| Reaction Time | Unreacted Benzyl Chloride (wt. %) | Isocyanate (wt. %) | Isocyanurate (wt. %) |
| --- | --- | --- | --- |
| 45 minutes | 41 | 55 | 4 |
| 4 hours | 0 | 73 | 23 |

From the above results, it is seen that the reaction rate was lower than in Example 1 and the amount of the isocyanurate formed as the by-product was larger at the time of the completion of the reaction, and that this process is not satisfactory when isolation of the isocyanate is desired.

COMPARATIVE EXAMPLE 2

The reaction was conducted in the same manner as described in Example 1 except that cuprous chloride was not added. The filtrate recovered from the reaction mixture obtained when the reaction was continued for 4.5 hours was found to comprise 18% of the isocyanate, 17% of the isocyanurate and 65% of the unreacted starting benzyl chloride. With the passage of the reaction time, the catalyst activity was drastically lowered.

COMPARATIVE EXAMPLE 3

Figure 2:
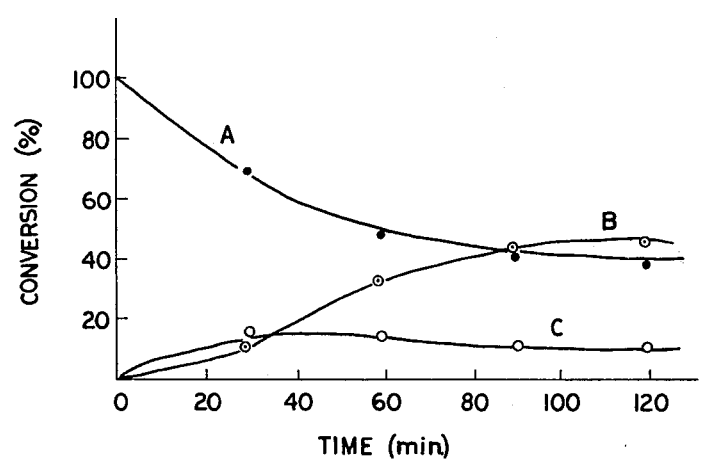
FIG. 2 is a graph illustrating the change of the composition of the reaction mixture, with the passage of time, for comparative Example 3.

A reaction vessel was charged with 19 g of benzyl chloride, 12.7 g of sodium cyanate, 66 g of o-dichlorobenzene and 1.4 g of trimethylbenzylammonium chloride, and the reaction was conducted under the same conditions as described in Example 1. The change of the composition of the reaction mixture with the lapse of time was as shown in FIG. 2. In FIG. 2, curves A, B and C indicate changes of contents of benzyl chloride, tribenzyl isocyanurate and benzyl isocyanate with the passage of time, respectively.

COMPARATIVE EXAMPLE 4

A reaction vessel was charged with 19 g of benzyl chloride, 12.7 g of sodium cyanate having a purity of 100%, 66 g of o-dichlorobenzene, 1.5 g of cuprous chloride and 1.7 g of triethylene diamine, and the reaction was carried out at 180° C for 45 minutes to complete the reaction. The inorganic salts were removed from the reaction mixture by filtration and the filtrate was analyzed. It was found that the filtrate comprised 5.0 g (25%) of benzyl isocyanate and 15.0 g (75%) of tribenzyl isocyanurate.

The embodiments of the invention in which an exclusive property or privilege is claimed are defined as follows:

1. A process for preparing organic isocyanates which comprises reacting at a temperature of from 150° to 250° C, for from 0.1 to 10 hours, an alkali metal or ammonium cyanate, or mixture thereof, with a compound having the formula

wherein X is chlorine, alkyl, cycloalkyl, alkenyl, phenyl, chloromethylphenyl or chloromethyl, n is zero or an integer of from 1 to 3 and R is an aromatic hydrocarbon radical, and X can be the same or different when n is more than 1, in the presence of a catalyst composition consisting essentially of (a) from 0.1 to 20 weight percent, based on the weight of said compound, of a cuprous salt selected from the group consisting of cuprous chloride, cuprous bromide, cuprous thiocyanate, cuprous cyanate and mixtures thereof, and (b) a nitrogen compound selected from the group consisting of triethylene diamine, pyridine, ethylpyridine, lutidine, collidine, trimethylamine, triethylamine, tripropylamine, tributylamine, triamylamine, trihexylamine, tri-higher-alkylamines, dimethylbenzylamine, methyldibenzylamine, tribenzylamine, dimethylnaphthylamine, N-methylpiperidine, N-methylmorpholine, N-butylmorpholine, N,N'-dimethylpiperazine, tetramethylammonium chloride, tetraethylammonium chloride, trimethylbenzylammonium chloride, dimethylbenzyl-higher-alkyl-ammonium chloride, tetramethylammonium bromide, tetraethylammonium bromide, trimethylbenzylammonium bromide, 1,8-diazabicyclo[5.4.0]-7-undecene and mixtures thereof, in an amount of said nitrogen compound equivalent to from 0.05 to 1.25 gram atoms of nitrogen per gram mole of said cuprous salt, and in a solvent, or mixture of solvents, having a dielectric constant (ε) of ≦ 20, which are free of active hydrogen atoms and which have a boiling point of from 150° to 400° C.

2. A process as claimed in claim 1 in which said cyanate is sodium cyanate or potassium cyanate.

3. A process as claimed in claim 2 in which said compound is benzyl chloride.

4. A process as claimed in claim 2 in which said compound is allyl chloride.

* * * * *

UNITED STATES PATENT AND TRADEMARK OFFICE
CERTIFICATE OF CORRECTION

PATENT NO. : 4 056 547
DATED : November 1, 1977
INVENTOR(S) : Yoshiaki Tanaka et al It is certified that error appears in the above-identified patent and that said Letters Patent are hereby corrected as shown below:

Column 6, line 37: After "radical" insert ---or a mono-olefinically unsaturated hydrocarbon radical---.

Signed and Sealed this

Twenty-first Day of February 1978

[SEAL]

Attest:

RUTH C. MASON
Attesting Officer

LUTRELLE F. PARKER
Acting Commissioner of Patents and Trademarks